United States Patent [19]

McNally

[11] 4,315,956

[45] Feb. 16, 1982

[54] PROCESS FOR DEPOSITING COBALT ONDES ON A REFRACTORY-COATED PLATINUM RESISTOR COIL

[75] Inventor: Frank X. McNally, Venetia, Pa.

[73] Assignee: National Mine Service Company, Pittsburgh, Pa.

[21] Appl. No.: 142,026

[22] Filed: Apr. 21, 1980

[51] Int. Cl.³ ............................................. B05D 3/14
[52] U.S. Cl. ................................. 427/52; 427/116; 427/126.6
[58] Field of Search ................. 204/290 R; 252/425.3, 252/466 J, 466 B; 422/96, 97; 427/49, 52, 103, 126.4, 126.6, 419.3

[56] References Cited

U.S. PATENT DOCUMENTS

| | | | |
|---|---|---|---|
| 4,045,177 | 8/1977 | McNally | 422/96 |
| 4,072,467 | 2/1978 | Jones | 422/97 |
| 4,125,449 | 11/1978 | Lewis et al. | 204/290 F |

*Primary Examiner*—W. J. Shine
*Attorney, Agent, or Firm*—Stanley J. Price, Jr.; John M. Adams

[57] ABSTRACT

An improvement is provided in a portable gas detector used to detect combustible gases, such as methane, which embodies a Wheatstone bridge circuit including a refractory-coated detector element having thereon a catalyst for promoting oxidation of the combustible gas to be detected constituting one leg of the bridge and a refractory-coated reference element constituting a second leg of the bridge. The improvement consists in the application of a cobalt oxide coating to the reference element, whereby the occurrence of spurious signals by the Wheatstone bridge circuit due to causes other than the presence of a combustible gas is greatly reduced, if not completely eliminated.

1 Claim, 1 Drawing Figure

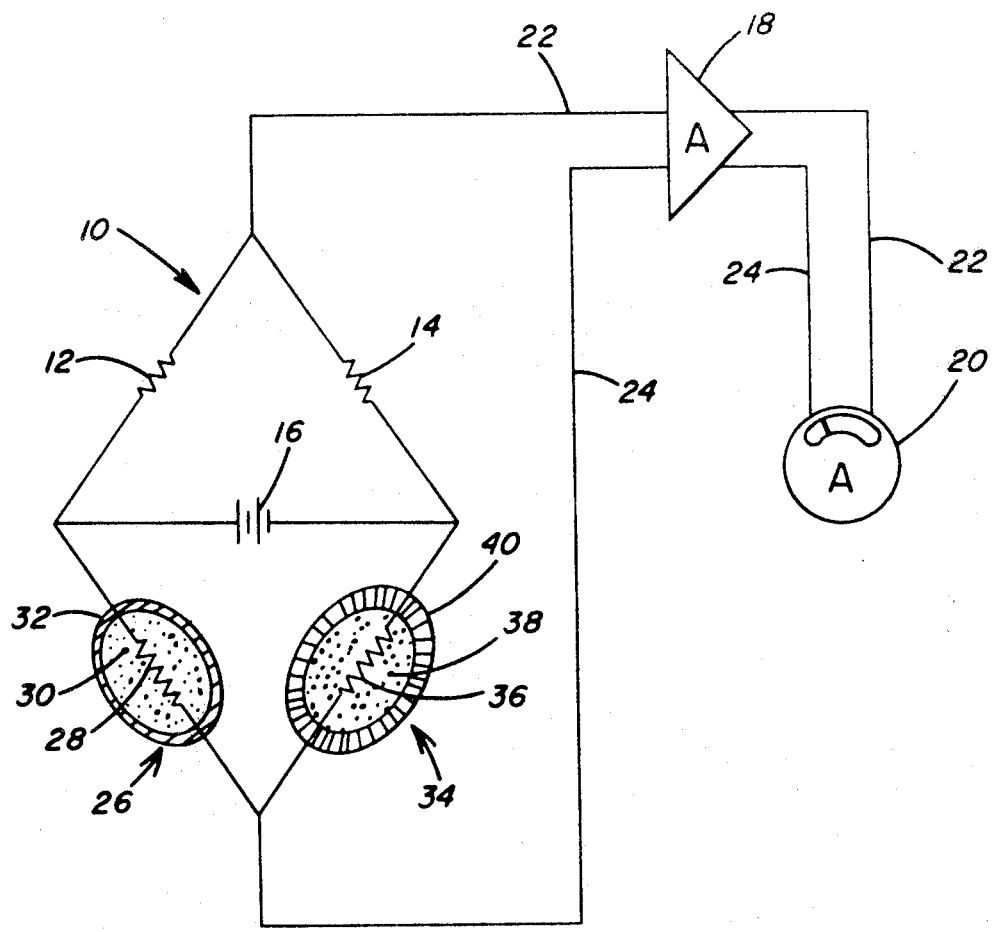

PROCESS FOR DEPOSITING COBALT ONDES ON A REFRACTORY-COATED PLATINUM RESISTOR COIL

This invention relates to an improvement in apparatus for detecting combustible gases such as methane.

Wheatstone bridge circuits are commonly used today for detection of combustible gases. For such use, the Wheatstone bridge circuit includes a refractory-coated detector element constituting one leg of the bridge and a refractory-coated reference element constituting a second leg of the bridge. These two elements comprise minute platinum coils coated with the refractory, for example, alumina, that is $Al_2O_3$. The detector element also has a catalytic coating formed upon the refractory coating, the purpose of which is to catalyze the reaction of combustible gases with oxygen. The catalytic coating contains a suitable catalyst such as platinum or palladium, or mixtures thereof. The reference element has a non-catalytic coating formed upon its refractory coating. Ideally, the function of this second coating of the reference element is to effectively nullify any changes in the detector element that would cause a spurious signal to be given by the Wheatstone bridge circuit of the presence of combustible gas. An additional function of the second coating on the reference element is to poison any catalytic effect of its refractory coating to promote the reaction which is catalyzed by the catalyst in the detector element.

There are many characteristics that must be possessed by the second coating of the reference element in order for it to perform its stated functions satisfactorily. These characteristics or properties are those which ideally nullify those changes in the detector element which result from changes in operating voltages, ambient temperature, humidity, aging and possibly others. To find a chemical composition suitable for use in such coatings is essentially an empirical undertaking. A few compositions have been reported that possess the desired characteristics to such extent that they are used commercially.

In accordance with my invention, I have found a chemical composition which I believe to be superior to any of those in commerical use today as the outer or second coating of the reference element described above. That chemical composition is a cobalt oxide, or a mixture of two of the cobalt oxides, CoO, and $Co_3O_4$. The cobalt oxide coating may be suitably formed by applying an aqueous solution of cobaltous nitrate, $Co(NO_3)_2$, to the refractory coating of the reference element, and thereafter heating the element to a temperature between 500° C. and 1000° C. in the presence of air until the desired oxide formation has occurred.

For a better understanding of my invention, its objects and advantages, reference should be had to the following description of the preferred embodiment and to the accompanying drawing which is a schematic showing of the preferred embodiment.

BRIEF DESCRIPTION OF THE DRAWING

The drawing illustrates the circuitry of the invention.

Referring to the drawing there is shown a Wheatstone bridge circuit generally designated by the numeral 10. The circuit has two fixed resistors 12 and 14 and a source of potential 16. The output from the circuit is connected through an amplifier 18 to an analogue meter 20 via conductors 22 and 24. The circuit includes a methane detector element designated generally by the numeral 26. This detector element comprises a platinum resistor coil 28 which has an alumina ($Al_2O_3$) refractory coating 30 over which is coated a catalyst for methane oxidation designated by the numeral 32. The catalyst for this preferred embodiment may be, alternatively, platinum, palladium, or a mixture of platinum and palladium. The circuit also includes a reference element designated generally by the numeral 34. The reference element comprises a platinum resistor coil 36 coated with an alumina refractory layer 38 over which is deposited a coating 40 of cobalt oxides as described below.

The coating 40 of cobalt oxides is formed as follows. An aqueous solution of cobaltous nitrate is made by dissolving cobaltous nitrate in water. This solution is suitably applied to the alumina refractory coating, and then heated to a temperature between 500° C. and 1000° C. in the presence of air by passing electrical current through the resistor 36 for sufficient time to convert the cobaltous nitrate to the oxides of cobalt. If necessary to obtain the requisite thickness of the oxide coating, the entire procedure may have to be repeated. The requisite thickness is established when the Wheatstone bridge circuit becomes insensitive to changes in bridge voltage.

The operation of the bridge circuit is as follows. By the suitable selection of resistors there is a zero output from the bridge circuit in the absence of methane at the detector element 26. In the presence of methane, the methane is oxidized at the detector element 26. The oxidation is promoted by the catalyst 32. Since the reaction of methane and oxygen is exothermic, the temperature of the detector element and accordingly of the platinum coil 28 is increased. The temperature of the platinum coil 36 of the reference element 34, however, remains unaffected as there is no oxidation of methane at this element. As the temperature of the detector element 26 increases, relative to the reference element 34, the resistance of coil 28 correspondingly increases relative to the resistance of the coil 36 of the reference element 34. Consequently, the bridge becomes unbalanced, and a signal is produced via the conductors 22 and 24 to amplifier 18. This signal is approximately proportional to the increase in resistance of the detector element 26 and accordingly to the oxidation of methane at the detector, which in turn is approximately proportional to the amount or concentration of methane in the atmosphere at the detector element. The signal is amplified by the amplifier 18 and transmitted to the analogue meter 20 which is suitably calibrated to provide a readout proportional to methane in the atmosphere.

EXPERIMENTAL SECTION

The object of the following reported experiment was to determine whether the use of a coating of cobalt oxides in the reference element in a Wheatstone bridge circuit as described above would prevent the development of spurious signals of methane presence when the bridge voltage was varied as is frequently the case in commercial units employing batteries as the source of power.

A solution was first prepared which had the following composition:

| | |
|---|---|
| Cobaltous Nitrate, $Co(NO_3)_2 \cdot 6H_2O$ | 0.582 grams |
| Distilled Water, $H_2O$, | 5 ml. |

This solution was then applied to the refractory consisting of aluminum oxide which enveloped the platinum coil of the reference element. The solution was dried and the cobaltous nitrate converted to oxides by passing a current through the reference element in the presence of air. The temperature of the element during the conversion to oxides was between 500° C. and 1000° C. The reference element was then placed in a Wheatstone bridge of the type shown in the drawing and described above, to determine the zero drift of the bridge signal in the absence of methane.

For purposes of comparison, the zero drift with voltage changes was determined for a circuit in which the reference element had no deposit of cobalt oxides. The results are reported below in Table I.

TABLE I

| Bridge Voltage | Bridge Signal | Instrument Display |
| --- | --- | --- |
| 2.6 Volts | −6.1 mV | −0.2% Methane |
| 2.4 Volts | 0.0 mV | 0.0% Methane |
| 2.2 Volts | +4.4 mV | +0.1% Methane |

One micro-liter of the cobaltous nitrate solution was then applied to the reference element and the element heated by passing current through the platinum coil as follows to form various cobalt oxides on the surface of the reference element:

| Current-mA | Time |
| --- | --- |
| 0–100 | 1 Min. |
| 100–200 | 1 Min. |
| 200–300 | 1 Min. |
| 300 | 1 Min. |

TABLE II

| | RESULTS: | |
| --- | --- | --- |
| Bridge Voltage | Bridge Signal | Instrument Display |
| 2.6 Volts | −3.7 mV | −0.1% Methane |
| 2.4 Volts | 0.0 mV | 0.0% Methane |
| 2.2 Volts | +3.2 mV | +0.1% Methane |

The sensitivity to bridge voltage has descreased. The coating application was repeated a second time.

TABLE III

| Bridge Voltage | Bridge Signal | Instrument Display |
| --- | --- | --- |
| 2.6 Volts | −2.7 mV | 0.0% Methane |
| 2.4 Volts | 0.0 mV | 0.0% Methane |
| 2.2 Volts | +2.6 mV | 0.0% Methane |

The coating application was repeated a third time.

TABLE IV

| | RESULTS: | |
| --- | --- | --- |
| Bridge Voltage | Bridge Signal | Instrument Display |
| 2.6 Volts | −1.6 mV | 0.0% Methane |
| 2.4 Volts | 0.0 mV | 0.0% Methane |
| 2.2 Volts | +1.4 mV | 0.0% Methane |

The detector now has sufficient insensitivity to bridge voltage change so that the instrument display in turn exhibits a zero change in % Methane when the bridge voltage changes.

This detector was then life-tested in a cycle consisting of 15 seconds on and 75 seconds off, the total cycle being 90 seconds. The detector was life-tested in this manner for a total of 75.5 hours, which is approximately equivalent to six months of field usage. At the end of this time detector was tested for bridge voltage sensitivity with the results as follows:

TABLE V

| Bridge Voltage | Bridge Signal | Instrument Display |
| --- | --- | --- |
| 2.6 Volts | −1.4 mV | 0.0% Methane |
| 2.4 Volts | 0.0 mV | 0.0% Methane |
| 2.2 Volts | +1.2 mV | 0.0% Methane |

There was no significant change in sensitivity.

According to the provisions of the Patent Statutes, I have explained the principle, preferred construction and mode of operation of my invention and have illustrated and described what I now consider to represent its best embodiments. However, it should be understood that, within the scope of the appended claims, the invention may be practiced otherwise than as specifically illustrated and described.

I claim:

1. A process for depositing cobalt oxides on a refractory-coated platinum resistor coil which comprises applying an aqueous solution of cobaltous nitrate to the surface of the refractory, passing a current through the conductor in the presence of air to raise its temperature to 500° C. to 1000° C., whereby the cobaltous nitrate is oxidized to cobalt oxides and the water is volatilized.

* * * * *